(12) United States Patent
Darscht et al.

(10) Patent No.: US 9,701,298 B2
(45) Date of Patent: Jul. 11, 2017

(54) METHOD AND DEVICE FOR ASCERTAINING AT LEAST ONE VARIABLE REGARDING A STATE OF A BRAKE FLUID IN A BRAKE SYSTEM OF A VEHICLE

(71) Applicant: Robert Bosch GmbH, Stuttgart (DE)

(72) Inventors: Wadim Darscht, Schwaebisch Hall (DE); Benjamin Ardouin, Stuttgart (DE); Daniel Frank, Kleinsachsenheim (DE); Cedric Pinard, Champigny sur Marne (FR)

(73) Assignee: Robert Bosch GmbH, Stuttgart (DE)

( * ) Notice: Subject to any disclaimer, the term of this patent is extended or adjusted under 35 U.S.C. 154(b) by 21 days.

(21) Appl. No.: 14/834,716

(22) Filed: Aug. 25, 2015

(65) Prior Publication Data
US 2016/0052501 A1 Feb. 25, 2016

(30) Foreign Application Priority Data
Aug. 25, 2014 (DE) .......... 10 2014 216 841

(51) Int. Cl.
*B60T 17/22* (2006.01)
*B60T 8/40* (2006.01)
(Continued)

(52) U.S. Cl.
CPC ............ *B60T 17/22* (2013.01); *B60T 8/4081* (2013.01); *G01F 1/00* (2013.01); *G01N 11/04* (2013.01);
(Continued)

(58) Field of Classification Search
CPC .. B60T 17/22; B60T 8/4081; B60T 2270/406; G01F 1/00; G01N 11/04
See application file for complete search history.

(56) References Cited

U.S. PATENT DOCUMENTS 5,187,666 A * 2/1993 Watanabe ............... B60T 8/172
180/197
5,887,955 A * 3/1999 Ando ........................ B60T 7/12
303/11

(Continued)

FOREIGN PATENT DOCUMENTS

DE 10 2009 028 542 A1 2/2011
FR 2967631 * 11/2010 ............ B60T 13/132

*Primary Examiner* — Calvin Cheung
(74) *Attorney, Agent, or Firm* — Norton Rose Fulbright US LLP; Gerard Messina

(57) ABSTRACT

A method and device for ascertaining at least one variable regarding a state of a brake fluid in a brake system of a vehicle includes a device determining a volume flow variable regarding a volume flow, which flows via a simulator separation valve into a simulator by taking into account at least one displacement speed variable regarding a displacement speed of a brake pedal/rod piston; determining a simulator internal pressure variable regarding a simulator internal pressure by taking into account at least one pedal travel variable regarding a pedal travel; determining a pressure difference variable regarding a pressure difference at the simulator separation valve by taking into account the simulator internal pressure variable and an admission pressure variable regarding an admission pressure; and determining at least one variable by taking into account the at least one determined volume flow variable and the at least one determined pressure difference variable.

20 Claims, 3 Drawing Sheets

(51) Int. Cl.
*G01F 1/00* (2006.01)
*G01N 11/04* (2006.01)
*G01F 3/16* (2006.01)
*G01N 11/08* (2006.01)

(52) U.S. Cl.
CPC .......... *B60T 2270/406* (2013.01); *G01F 3/16* (2013.01); *G01N 11/08* (2013.01)

(56) References Cited

U.S. PATENT DOCUMENTS

| | | | | |
|---|---|---|---|---|
| 6,024,420 A * | 2/2000 | Yonemura | ............... | B60T 7/12 |
| | | | | 303/113.2 |
| 6,254,198 B1 * | 7/2001 | Zittlau | ............... | B60T 13/741 |
| | | | | 303/113.4 |
| 6,345,869 B1 * | 2/2002 | Matsuo | ............... | B60T 8/268 |
| | | | | 303/113.1 |
| 6,901,789 B1 * | 6/2005 | Fennel | ............... | B60T 8/368 |
| | | | | 701/70 |
| 8,706,358 B2 * | 4/2014 | DeWitt | ............... | B60T 1/10 |
| | | | | 180/197 |
| 9,233,676 B2 * | 1/2016 | Ullrich | ............... | B60T 1/10 |
| 2001/0006306 A1 * | 7/2001 | Kagawa | ............... | B60T 8/367 |
| | | | | 303/20 |
| 2002/0008426 A1 * | 1/2002 | Isono | ............... | B60T 8/367 |
| | | | | 303/115.4 |
| 2002/0129644 A1 * | 9/2002 | Petty | ............... | G01N 21/293 |
| | | | | 73/61.46 |
| 2006/0158033 A1 * | 7/2006 | Ohkubo | ............... | B60T 8/36 |
| | | | | 303/191 |
| 2007/0159001 A1 * | 7/2007 | Miyazaki | ............... | B60T 8/4081 |
| | | | | 303/113.4 |
| 2008/0265662 A1 * | 10/2008 | Karnjate | ............... | B60T 7/06 |
| | | | | 180/65.27 |
| 2009/0230761 A1 * | 9/2009 | Sekiguchi | ............... | B60T 8/442 |
| | | | | 303/2 |
| 2009/0243382 A1 * | 10/2009 | Yamauchi | ............... | B60T 8/36 |
| | | | | 303/155 |
| 2010/0269683 A1 * | 10/2010 | Anderson | ............... | B60T 7/042 |
| | | | | 91/369.1 |
| 2011/0071743 A1 * | 3/2011 | Taniguchi | ............... | B60T 8/36 |
| | | | | 701/70 |
| 2013/0080016 A1 * | 3/2013 | Bohn | ............... | B60T 7/042 |
| | | | | 701/78 |
| 2013/0342005 A1 * | 12/2013 | Baumann | ............... | B60T 8/4031 |
| | | | | 303/10 |
| 2014/0008965 A1 * | 1/2014 | Ito | ............... | B60T 8/4081 |
| | | | | 303/3 |
| 2014/0142810 A1 * | 5/2014 | Watanabe | ............... | B62D 5/0481 |
| | | | | 701/41 |
| 2014/0305751 A1 * | 10/2014 | Yamamoto | ............... | B60T 8/00 |
| | | | | 188/72.4 |
| 2015/0158471 A1 * | 6/2015 | Ezoe | ............... | B60T 7/22 |
| | | | | 701/70 |

* cited by examiner

METHOD AND DEVICE FOR ASCERTAINING AT LEAST ONE VARIABLE REGARDING A STATE OF A BRAKE FLUID IN A BRAKE SYSTEM OF A VEHICLE

FIELD OF THE INVENTION

The present invention relates to a method for ascertaining at least one variable regarding a state of a brake fluid in a brake system of a vehicle. The present invention also relates to a device for ascertaining at least one variable regarding a state of a brake fluid in a brake system of a vehicle. In addition, the present invention relates to a brake system for a vehicle.

BACKGROUND

DE 10 2009 028 542 A1 describes a method and a device for controlling a brake system. When using the device, or when implementing the method, a portion of the brake system is hydraulically decoupled from the remaining portion of the brake system, upon which a pressure change in the decoupled portion of the brake system resulting from a volume displacement in the decoupled portion is ascertained and evaluated for the purpose of determining a p-V characteristic curve (pressure-volume characteristic curve). The brake system is controlled based on the obtained p-V characteristic curve of the decoupled portion of the brake system.

SUMMARY

The present invention facilitates a simple and reliable ascertainment of at least one variable regarding a state of a brake fluid in a brake system of a vehicle. The present invention facilitates, in particular, determining reliably and with great accuracy variables that impair the flow properties of the valves/valve seats of a brake system such as, for example, viscosity, temperature, water content, an aging state, and/or (chemical) composition, of the brake fluid. Knowing the flow properties obtained in this manner makes it possible to optimize a dynamic performance of control signals output to the brake system. The present invention is therefore able to contribute significantly toward optimizing an operation of the brake system.

The present invention facilitates performing a regular/continual update of the at least one variable during an operation of the brake system. The regularly/continually performed update can subsequently be used for adapting the control signals output to the brake system to a changed property or a changed physical variable of the brake fluid.

The present invention can also be used in particular to optimize a characteristic of a brake pedal in such a way that a driver has an agreeable feeling of the pedal when actuating the brake pedal. The present invention can be used in particular to suppress influences of valves and lines, which may impair the pedal feel particularly at low temperatures. For this purpose, the at least one ascertained variable can be taken into account during every actuation of the brake pedal when controlling the individual components of the brake system. Above all, an ascertained viscosity of the brake fluid can be used advantageously as the at least one ascertained variable in order to prevent an occurrence of changes in the pedal feel.

In an example embodiment, a method includes determining, as the at least one variable, a viscosity, temperature, water content, aging state, and/or composition, of the brake fluid. These listed variables are able to be determined with a relatively high accuracy and a comparatively low risk of error. When determining any of the listed variables, it is possible to dispense with the use of an additional sensor, which is not designed for ascertaining the displacement speed variable, the pedal travel variable, or the admission pressure variable. In particular, it is possible to dispense with the use of a temperature sensor and a chemical detection sensor.

In an example embodiment, a volume flow Q is determined as the volume flow variable as follows:

$$Q = v_0 * \Phi,$$

where $v_0$ is the displacement speed of a rod piston and $\Phi$ is a braking surface of the rod piston. This makes it possible to determine volume flow Q in a comparatively simple manner.

A simulator internal pressure can also be determined as the simulator internal pressure variable by taking into account the pedal travel of the brake pedal as the pedal travel variable and a pedal travel-simulator internal pressure relation specified for the simulator. This eliminates the need to attach a separate pressure sensor to the brake system in order to determine the simulator internal pressure variable. The present invention thus contributes toward reducing the required installation space and the manufacturing costs for a brake system.

Preferably, at least one single value $v_i$ is determined for the viscosity of the brake fluid as the at least one variable by taking into account the volume flow Q as the volume flow variable and the pressure difference $\Delta p$ between the admission pressure and the simulator internal pressure as the pressure difference variable, as follows:

$$v_i = \frac{1}{A}\left(\frac{\Delta p}{\rho * Q} - B * Q\right),$$

where $\rho$ is a density of the brake fluid, A is a specified pressure loss parameter and B is a specified pressure drop parameter. The equation indicated here is easy to evaluate. In addition, the equation makes it possible to determine at least single values $v_i$ for the viscosity with high accuracy and a low error rate.

The viscosity of the brake fluid is preferably determined as an average value of multiple single values $v_1$. For example, during the single actuation of the brake pedal, it is possible to determine at most the one single value $v_1$. In an example embodiment, a subsequent formation of an average value from multiple single values $v_i$ is used to ensure that turbulences unexpectedly occurring in the brake fluid have hardly any influence on the determined viscosity of the brake fluid.

In addition, in an example embodiment, the pressure loss parameter and the pressure drop parameter are specified by using two calibration measurements with brake fluid of different viscosities. Since the pressure loss parameter and the pressure drop parameter remain (nearly) constant during the entire operation/the entire service life of the brake system, it suffices to perform two calibration measurements.

The advantages described above are also ensured in a corresponding device for ascertaining at least one variable regarding a state of a brake fluid in a brake system of a vehicle.

Furthermore, a brake system for a vehicle having a device of this type also provides the advantages explained above.

Additional features and advantages of the present invention are elucidated below with reference to the figures.

DETAILED DESCRIPTION

It is possible to implement the method described below in any brake system of a vehicle/motor vehicle, which has a simulator (e.g., a pedal simulator, a pedal travel simulator, or a pedal lift simulator), which is connected via a simulator separation valve (SSV) to a master brake cylinder of the same brake system in such a way that, by an actuation of a connected brake pedal, brake fluid is transferable from the master brake cylinder via the simulator separation valve into the simulator. Implementation of the method described below is limited neither to a specific type of brake system nor to a specific vehicle type/motor vehicle type. Furthermore, implementation of the method depends neither on a specific valve type of the simulator separation valve nor on a specific simulator type of the simulator. It is thus possible to use alternatively a separating valve or a regulating valve as the simulator separation valve in the brake system. A characteristic curve of the simulator can also be chosen with great freedom of design. Moreover, it makes no difference whether there is a short or a long connection between the simulator and the simulator separation valve or between a rod piston of the brake system and the simulator separation valve.

Figure 1A:
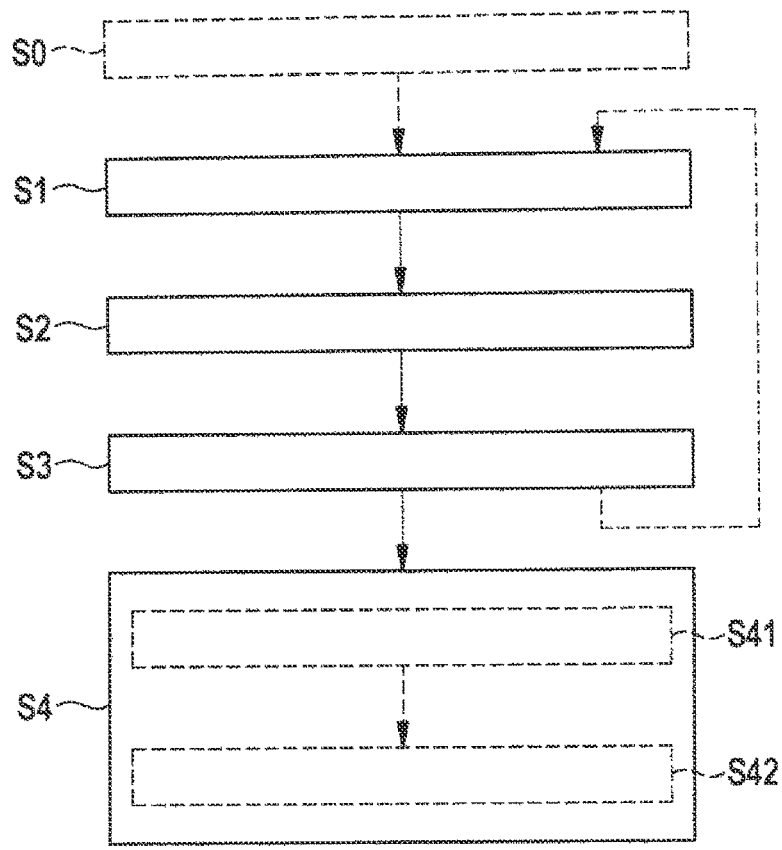
FIGS. 1a-1c include a flowchart and two coordinate systems for elucidating a specific embodiment of the method for ascertaining at least one variable regarding a state of a brake fluid in a brake system of a vehicle.

Referring to FIG. 1a, in an example embodiment, a method includes a step S1 in which a volume flow variable is determined regarding a volume flow Q that flows via the simulator separation valve into the simulator of the brake system when the brake pedal of the brake system is actuated. The volume flow variable is determined by taking into account at least one displacement speed variable regarding a displacement speed $v_p$ of the brake pedal and/or a displacement speed $v_0$ of a rod piston of the brake system displaced by the actuation of the brake pedal. The displacement speed variable can be for example the displacement speed $v_p$ of the brake pedal, the displacement speed $v_0$ of the rod piston, and/or at least one variable corresponding to the displacement speed $v_p$ of the brake pedal and/or the displacement speed $v_0$ of the rod piston. In particular, the displacement speed variable can be/indicate a time derivation of a pedal angle, possibly detected by a brake pedal angle sensor.

For example, volume flow Q can be determined as the volume flow variable in accordance with the following equation (Eq. 1):

$$Q = v_0 * \Phi, \quad \text{(Eq. 1)}$$

where $\Phi$ is a braking surface of the rod piston. The braking surface $\Phi$ of the rod piston can be easily stored in a memory unit.

In a brake system, there is frequently a constructionally/mechanically predetermined and (nearly) aging-independent relationship between displacement speed $v_p$ of the (actuated) brake pedal and the displacement speed $v_0$ of the rod piston of the brake system that is also displaced by the actuation of the brake pedal. In this case, it is easy to determine the constructionally/mechanically predetermined and (nearly) aging-independent relationship between the displacement speed $v_p$ of the brake pedal and the (resulting) displacement speed $v_0$ of the rod piston and to store it in the memory unit. (The displacement speed $v_0$ of the rod piston can in particular equal the displacement speed $v_p$ of the brake pedal.) Subsequently, the displacement speed $v_0$ of the rod piston can be reliably derived from the displacement speed $v_p$ of the brake pedal. (The displacement speed $v_p$ of the brake pedal can be derived in a simple manner and at a low error rate from a sensor signal of a sensor for ascertaining a pedal travel $x_p$, such as for example a pedal travel sensor (pedal lift sensor) and/or a rod travel sensor. The procedure described here thus also increases the usability of the sensor used to ascertain pedal travel $x_p$.)

Alternatively, displacement speed $v_0$ of the rod piston can also be specified/triggered by a brake booster of the brake system such as, e.g., an electromechanical brake booster of the brake system. (In particular, the brake booster can take into account the pedal travel $x_p$ and/or the displacement speed $v_p$ of the brake pedal in a specification of the displacement speed $v_0$ of the rod piston. In this case as well, no measurement of displacement speed $v_0$ of the rod piston is necessary. Instead, it is possible for control electronics of the brake booster to output an information signal regarding the displacement speed $v_0$ without additional effort. Thus, in this case as well, no specifically designed sensor is required for determining the displacement speed $v_0$ of the rod piston.

For this reason, the volume flow variable can also be determined in method step S1 by (additionally) taking into account a displacement speed variable regarding the displacement speed $v_p$ of the brake pedal.

If desired, it is possible to filter the sensor signal regarding the pedal travel $x_p$, a signal derived from it for the displacement speed $v_0$ of the rod piston or the information signal.

A simulator internal pressure variable regarding a simulator internal pressure $p_s$, which has been elevated due to volume flow Q into the simulator, is determined in a method step S2. The simulator internal pressure variable is determined by taking into account at least one pedal travel variable regarding the pedal travel $x_p$ of the brake pedal. The simulator internal pressure $p_s$ or a variable corresponding to simulator internal pressure $p_s$ can be determined as the simulator internal pressure variable in method step S2. The pedal travel variable can also indicate a pedal angle and/or an angle/angle of rotation of a motor component/thread component of an electromechanical brake booster. The simulator internal pressure $p_s$ (as the simulator internal pressure variable) is advantageously determined by taking into account the pedal travel $x_p$ of the brake pedal (as the pedal travel variable) and a pedal travel-simulator internal pressure relationship specified for the simulator (and possibly stored in the memory unit).

Figure 1B:
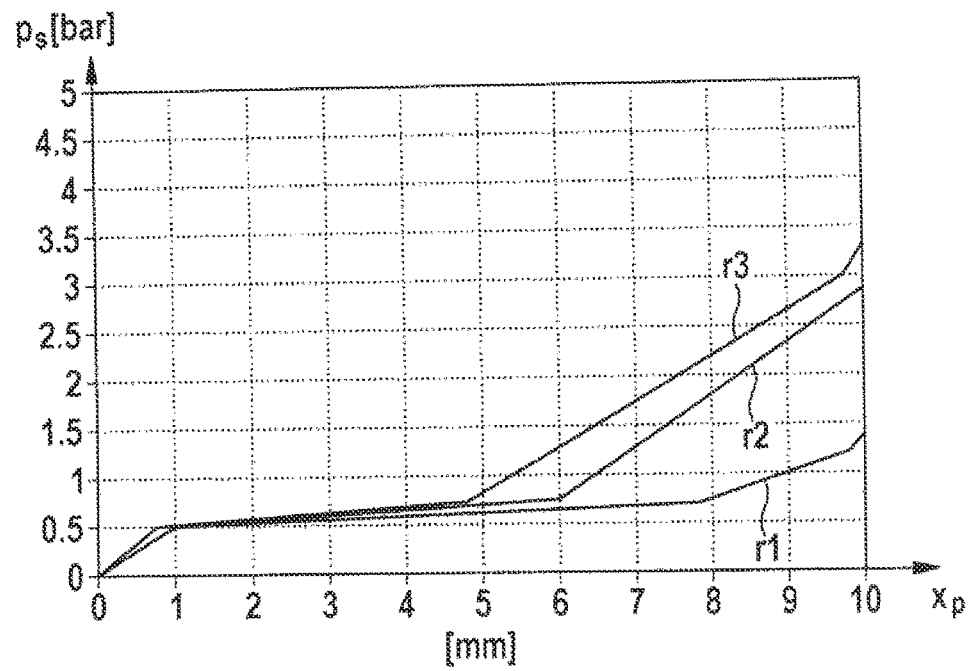

FIG. 1b shows a coordinate system, the abscissa of which represents a pedal travel $x_p$ of the brake pedal (in millimeters) and the ordinate of which represents a simulator internal pressure $p_s$ (in bars). Possible pedal travel-simulator internal pressure relations r1 through r3 are plotted in the coordinate system of FIG. 1b by way of example. It is thus also possible to perform method step S2 in a comparatively simple manner. The pedal travel-simulator internal pressure relations r1 through r3 plotted in the coordinate system of FIG. 1b, however, are to be interpreted only in exemplary fashion.

Simulator internal pressure $p_s$ can thus be reliably determined even without the use of a pressure sensor on/in the simulator. In particular, to determine the simulator internal pressure $p_s$, it is only necessary to ascertain pedal travel $x_p$ using a suitable sensor and to store a suitable pedal travel-simulator internal pressure relation in the memory unit. A pedal travel sensor (pedal lift sensor) and/or a rod travel sensor are non-exclusive examples of sensors suitable for reliably determining pedal travel $x_p$. Since a pedal travel sensor or a rod travel sensor is often already built into the brake system, method step S2 can be performed also without equipping the brake system with an additional sensor.

In method step S3, a pressure difference variable is determined regarding a pressure difference $\Delta p$, which exists at the simulator separation valve through which the volume flow flows. The pressure difference variable is determined by taking into account the simulator internal pressure variable determined for the respective volume flow Q and an admission pressure variable ascertained for the respective volume flow Q regarding an admission pressure $p_0$ prevailing at the simulator separation valve, through which volume flow Q flows, on a side that is facing away from the simulator. In particular, the pressure difference $\Delta p$, which prevails at the simulator separation valve through which the volume flow flows, can be determined as the pressure difference variable in accordance with the following equation (Eq. 2):

$$\Delta p = p_0 - p_s. \quad \text{(Eq. 2)}$$

Normally, at least one pressure sensor suitable for determining admission pressure $p_0$ is already built into the brake system. The pressure sensor/admission pressure sensor suitable for determining admission pressure $p_0$ can be installed in particular (directly) on the side of the simulator separation valve facing away from the simulator. No additional sensor system is therefore required for carrying out method step S3. It should be pointed out, however, that instead of pressure difference $\Delta p$, it is also possible to ascertain another variable corresponding to the pressure difference $\Delta p$ as the pressure difference variable in method step S3.

The method steps S1-S3 described above are carried out at least once. Subsequently, in a method step S4, the at least one variable regarding the state of the brake fluid is determined by taking into account the at least one determined volume flow variable and the at least one determined pressure difference variable.

Advantageously, a viscosity v, temperature, water content, aging state, and/or (chemical) composition, of the brake fluid is/are determined as the at least one variable. These, however, are merely examples of the at least one variable.

Method steps S1-S4 thus utilize the throttle effect at the simulator separation valve to determine the at least one variable without an additional sensor system. When carrying out method steps S1-S3, use may be made especially of sensors, such as a pedal travel sensor and an admission pressure sensor for example, that are usually already installed in the vehicle. Performing method steps S1-S4 thus makes additional sensors in the brake system superfluous for measuring the viscosity v, temperature, water content, aging state, and/or (chemical) composition, of the brake fluid, which contributes toward reducing a required installation space and the manufacturing costs of a brake system operated in part by method steps S1-S4. Furthermore, compared to the sensors conventionally used for this purpose, method steps S1-S4 allow for a more accurate and more error-free determination of the viscosity v, temperature, water content, aging state, and/or (chemical) composition, of the brake fluid.

The viscosity v, temperature, water content, aging state, and/or (chemical) composition, of the brake fluid determined in method step S4 can subsequently be also taken into account for a plurality of control processes when operating the brake system. This improves the operation of the brake system.

Figure 1C:
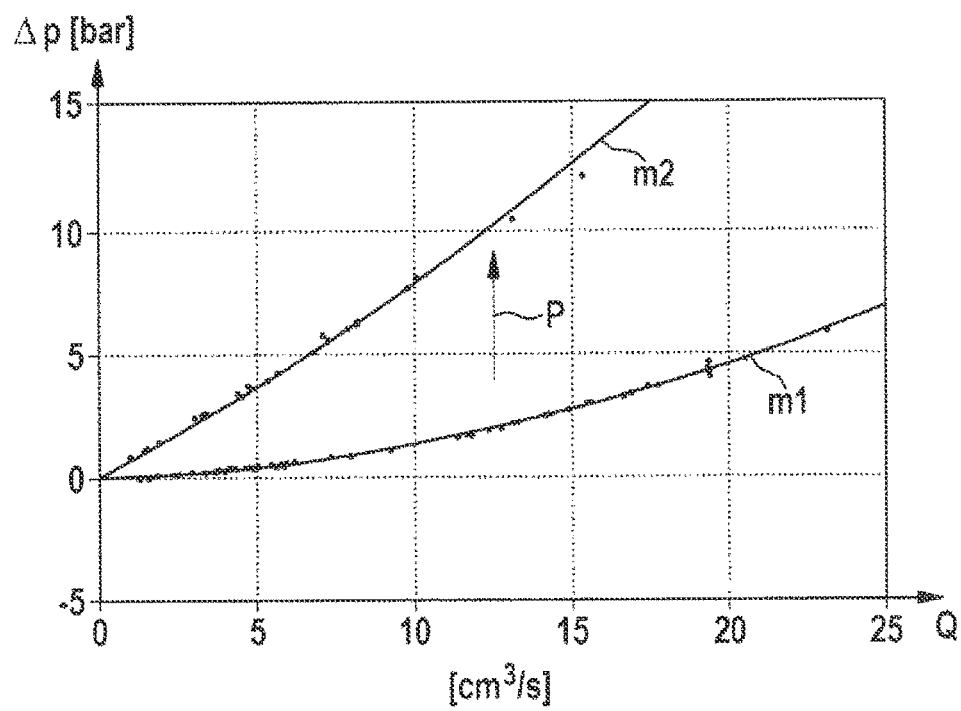

In the specific embodiment of FIGS. 1a-1c, a single value $v_i$ is determined in a sub-step S41 for the viscosity v of the brake fluid by taking into account volume flow Q as the volume flow variable and pressure difference $\Delta p$ (between admission pressure $p_0$ and simulator internal pressure $p_s$) as the pressure difference variable in accordance with equation (Eq. 3):

$$v_i = \frac{1}{A}\left(\frac{\Delta p}{\rho * Q} - B * Q\right), \quad \text{(Eq. 3)}$$

where $\rho$ is a density of the brake fluid, A is a specified pressure loss parameter, and B is a specified pressure drop parameter. Subsequently, viscosity v of the brake fluid is determined in another sub-step S42 as the average value of multiple single values $v_i$. Instead of a single value $v_i$, however, it is also possible to determine the viscosity v itself using equation (Eq. 3).

Pressure loss parameter A normally depends on a length $L_1$ and a diameter $D_1$ of a line extending from the simulator separation valve to the simulator. Assuming a laminar flow of the brake fluid through the respective line, pressure loss parameter A is proportional to length $L_1$ of the line and inversely proportional to the fourth power of diameter $D_1$ of the line. Pressure loss parameter A is normally defined in accordance with equation (Eq. 4), as follows:

$$A = \frac{128 * L_l}{\pi * D_l^4} \quad \text{(Eq. 4)}$$

Pressure drop parameter B depends essentially on a throttle diameter $D_s$ of the simulator separation valve and on a throttle factor $K_s$ of the simulator separation valve. (Diameter $D_1$ of the line (approximately 6 mm) has a negligible influence on throttling the brake fluid compared to throttle diameter $D_s$ of the simulator separation valve (approximately 0.9 mm).) Pressure drop parameter B is usually derivable in accordance with equation (Eq. 5), as follows:

$$B = \frac{8 * K_S}{\pi^2 * D_S^4} \quad \text{(Eq. 5)}$$

Equation (Eq. 5) is valid particularly at room temperature.

Optionally, in an example embodiment, a method step S0 is performed prior to the first performance of method steps S1-S4. In optional method step S0, two calibration measurements can be performed using brake fluids that have different viscosities v. Subsequently, pressure loss parameter A and pressure drop parameter B can be specified by evaluating the two calibration measurements. Pressure loss parameter A and pressure drop parameter B can be subsequently stored in the memory unit, and can be downloaded from the memory unit for carrying out sub-step S41.

FIG. 1c shows a coordinate system, the abscissa of which represents a volume flow Q (in cubic centimeters per second) and the ordinate of which represents a pressure difference $\Delta p$ (in bars). Each of the averaged measurement curves m1 and m2 represents a calibration measurement, arrow P illustrating the viscosity increase between the two calibration measurements. The averaged measurement curves m1 and m2 can subsequently be used for determining pressure loss parameter A and pressure drop parameter B.

Pressure loss parameter A and pressure drop parameter B can thus be determined experimentally during the development of the brake system. It is also possible to determine density $\rho$ of the brake fluid experimentally. Frequently, it is also possible to store a value from the literature in the memory unit for the density $\rho$ of the brake fluid.

In a particularly advantageous example embodiment of the method, method steps S1-S3 are executed only/at most once during a (single) actuation of the brake pedal. In this manner, it is possible to use particularly the initial pressure build-up phase during the actuation of the brake pedal for determining the volume flow variable and the pressure difference variable. A false determination of the volume flow variable or the pressure difference variable is in this case relatively improbable. If desired, the at least one variable to be determined can be determined following a firmly specified number of actuations of the brake pedal. (The determination of the at least one variable is started for the first time, e.g., in an ignition cycle.)

Optionally, a time interval between two actuations of the brake pedal can be ascertained, for example, in a simple manner using a counter, which is started at each release of the brake pedal. Optionally, method steps S1-S3 are performed during the subsequent actuation of the brake pedal only if the ascertained time interval is greater than a specified minimum time interval, e.g., greater than a minimum interval of 15 seconds.

If desired, it is also possible to ascertain a temperature of the brake fluid and/or an ambient temperature in an environment of the brake system prior to carrying out method steps S1-S4. Subsequently, the ascertained temperature and/or the determined ambient temperature can be compared to at least one specified normal value range. In one possible example embodiment of the described method, method steps S1-S3 are performed only if the ascertained temperature and/or the determined ambient temperature lie(s) within the respective normal value range.

In an alternative example embodiment, method steps S1-S4 are performed (completely) only if the displacement speed $v_0$ of the rod piston and/or the displacement speed $v_p$ of the brake pedal lie within at least one specified normal value range of the speed. The respective normal value range of the speed can be limited by definitely specified speed limit values, such as for example a lower speed limit value at 1 mm/s and/or an upper speed limit value at 50 mm/s. The lower speed limit value and/or the upper speed limit value can also be specified as a function of the temperature of the brake fluid and/or the ambient temperature.

Accordingly, a (complete) execution of method steps S1-S4 can also be omitted if pedal travel $x_p$ lies outside of a specified pedal travel normal value range. The pedal travel normal value range can also be limited by firmly specified pedal travel limit values such as for example a lower pedal travel limit value at 2 mm and/or an upper pedal travel limit value at 7 mm. Alternatively, however, the lower pedal travel limit value and/or the upper pedal travel limit value can also be specified as a function of the temperature of the brake fluid and/or the ambient temperature.

Figure 2:
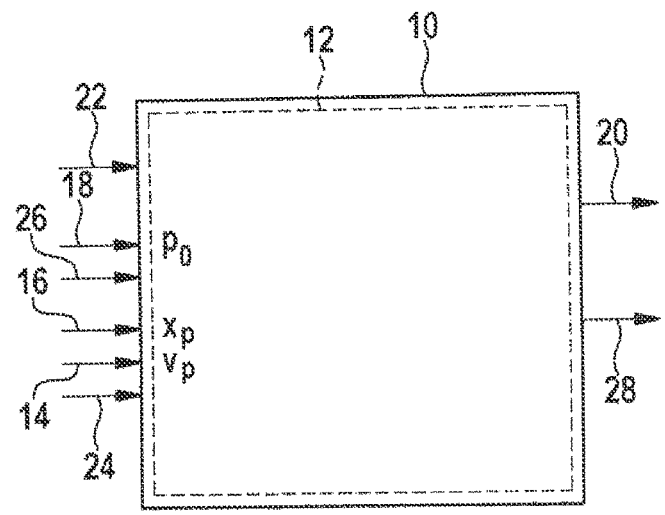
FIG. 2 shows a schematic representation of an example embodiment of a device for ascertaining at least one variable regarding a state of a brake fluid in a brake system of a vehicle.

FIG. 2 shows a schematic representation of a first example embodiment of a device for ascertaining at least one variable regarding a state of a brake fluid in a brake system of a vehicle.

The device 10 shown schematically in FIG. 2 includes an evaluation unit 12, which is designed to determine a volume flow variable regarding a volume flow Q, which flows via a simulator separation valve into a simulator of the brake system when a brake pedal of the brake system is actuated. The volume flow variable is determined by taking into account at least one ascertained or provided displacement speed variable 14 regarding a displacement speed $v_p$ of the brake pedal and/or a displacement speed $v_0$ of a rod piston of the brake system displaced by the actuation of the brake pedal.

In addition, evaluation unit 12 is configured to determine a simulator internal pressure variable regarding a simulator internal pressure $p_s$ increased as a result of volume flow Q into the simulator by taking into account at least one ascertained or provided pedal travel variable 16 regarding a pedal travel $x_p$ of the brake pedal. Furthermore, evaluation unit 12 is configured to determine a pressure difference variable regarding a pressure difference $\Delta p$, which prevails at the simulator separation valve through which volume flow Q flows. The pressure difference variable is determined by taking into account the simulator internal pressure variable determined for the respective volume flow Q and an admission pressure variable 18 ascertained or provided for the respective volume flow Q regarding an admission pressure $p_0$ prevailing at the simulator separation valve, through which volume flow Q flows, on a side that is facing away from the simulator.

Evaluation unit 12 is configured to determine subsequently the at least one variable by taking into account the at least one determined volume flow variable and the at least one determined pressure difference variable. Evaluation unit 12 can be used for example to determine a viscosity v, temperature, water content, aging state, and/or (chemical) composite, of the brake fluid as the at least one variable. Evaluation unit 12 is configured to thereupon output an output signal 20 corresponding to the at least one determined variable.

The evaluation of the variables 14-18 provided to device 10 occurs only during an actuation of the brake pedal (for example by the driver or by the electromechanical brake booster). Evaluation unit 12 is able to detect the actuation of the brake pedal for example by way of a provided pedal actuation signal 22.

Sensors for ascertaining variables 14-18 were already listed above. In an example embodiment, evaluation unit 12 is additionally configured to check/detect an operativeness of the at least one sensor for ascertaining the variables 14-18 by way of at least one quality signal 24 and 26 such as, e.g., a quality signal 24 of a pedal travel sensor and/or a quality signal 26 of an admission pressure sensor. Optionally, device 10/evaluation unit 12 is also configured to indicate its own operativeness by outputting a quality signal 28 of its own.

Figure 3:
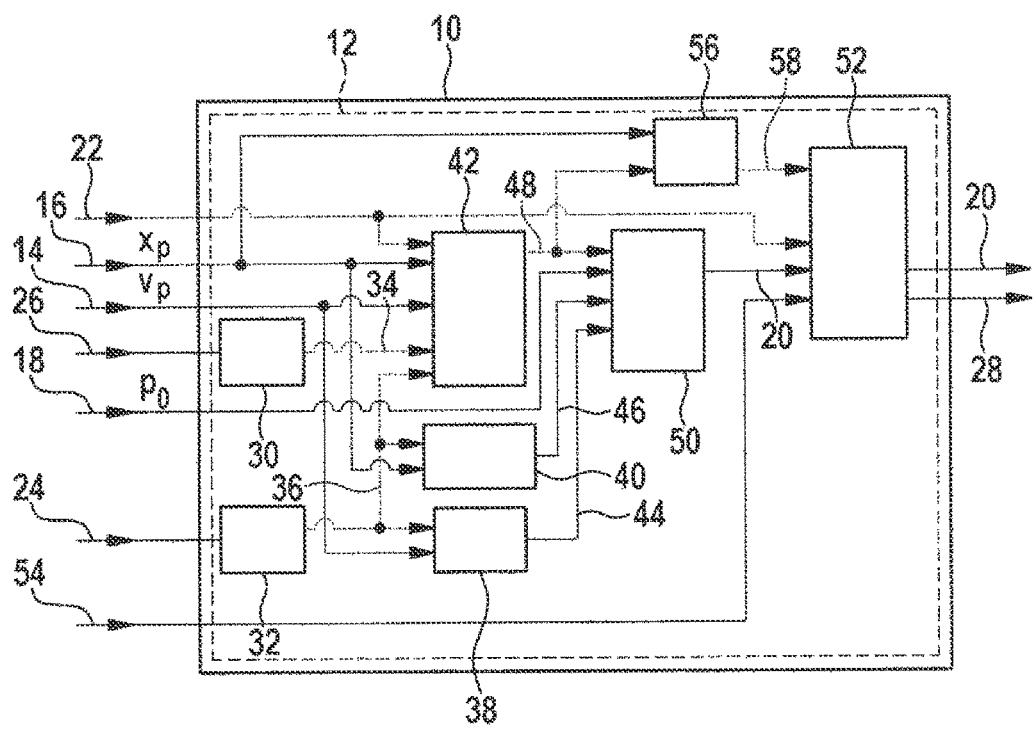
FIG. 3 shows a schematic representation of the device for ascertaining at least one variable regarding a state of a brake fluid in a brake system of a vehicle, with additional details, according to an example embodiment of the present invention.

FIG. 3 shows additional details of the device according to an example embodiment of the present invention. In the example embodiment of FIG. 3, the provided quality signals 24 and 26 of the pedal travel sensor and the admission pressure sensor are checked in exemplary fashion by respective checking subunits 30 and 32 of evaluation unit 12.

Checking subunits 30 and 32 subsequently output appropriate verification signals 34 and 36 to processing subunits 38-42 of evaluation unit 12.

Processing device 38 of the evaluation unit is configured to determine volume flow Q as the volume flow variable 44. This occurs in accordance with equation (Eq. 6), as follows:

$$Q = v_p * \Phi_p, \tag{Eq. 6}$$

where $v_p$ is the displacement speed of the brake pedal and $\Phi_p$ is a braking surface of the brake pedal.

Using processing subunit 40 of evaluation unit 12, it is possible to determine the simulator internal pressure $p_s$ as the simulator internal pressure variable 46 by taking into account the pedal travel $x_p$ of the brake pedal as the pedal travel variable 16 and a pedal travel-simulator internal pressure relation specified for the simulator. Processing subunit 42 checks signals 22, 34 and 36 and ascertains whether variables 14 and 16 lie within specified normal value ranges. If processing subunit 42 detects no deviations, then it outputs a verification signal 48 to another processing subunit 50 of evaluation unit 12.

Processing subunit 50 is designed to determine output signal 20. For example, processing subunit 50 of evaluation unit 12 is able to determine at least one single value $v_i$ for the viscosity v of the brake fluid as the at least one variable by taking into account volume current Q as volume flow variable 44 and pressure difference Δp from admission pressure $p_0$ (as admission pressure 18) and simulator internal pressure $p_s$ as pressure difference variable 46 in accordance with equation (Eq. 3). In particular, during the single actuation of the brake pedal, it is possible to determine only/at most one single value $v_i$. This is controllable by processing subunit 42. Subsequently, viscosity v of the brake fluid can be determined as an average value of multiple single values $v_i$.

Optionally, evaluation unit 12/device 10 additionally includes a signal output subunit 52 for outputting output signal 20 and quality signal 28 based further on at least one temperature signal 54. For this purpose, signals 20 and 22 are transmitted to signal output subunit 52, and at least one temperature signal 54 regarding a temperature of the brake fluid and/or an ambient temperature can likewise be provided to signal output subunit 52. Alternatively or additionally, another processing subunit 56 can check a plausibility of pedal travel variable 16 using signal 22 and, if applicable, output a corresponding verification signal 58 to signal output subunit 52.

The devices 10 explained above can also be designed for carrying out more of the previously described method steps. Another description of these method steps is omitted here.

All of the devices 10 described above are usable in a plurality of different types of brake systems. The components of the brake system interacting with the respective device 10, such as for example the simulator or the simulator separation valve, can be developed with great freedom of design. It should also be pointed out that the usability of each of the above-described devices 10 is also not limited to a specific vehicle type/motor vehicle type.

What is claimed is:

1. A method for ascertaining at least one variable regarding a state of a brake fluid in a brake system of a vehicle, the method comprising:

determining, by processing circuitry and using sensor signals, a volume flow variable regarding a volume flow Q of the brake fluid, which flows via a simulator separation valve into a simulator of the brake system during an actuation of a brake pedal of the brake system, based on at least one displacement speed variable regarding at least one of: (a) a displacement speed $v_p$ of the brake pedal of the brake system due to the actuation of the brake pedal, or (b) a displacement speed $v_0$ of a rod piston of the brake system displaced by the actuation of the brake pedal;

determining, by the processing circuitry and using sensor signals, a simulator internal pressure variable regarding a simulator internal pressure increased as a result of the volume flow Q into the simulator based on at least one pedal travel variable regarding a pedal travel of the brake pedal;

determining, by the processing circuitry, a pressure difference variable regarding a pressure difference Δp, which prevails at the simulator separation valve, through which the volume flow Q flows, based on the simulator internal pressure variable determined for the respective volume flow Q and an admission pressure variable ascertained for the respective volume flow Q regarding an admission pressure prevailing at the simulator separation valve, through which volume flow Q flows, on a side that is facing away from the simulator;

determining, by the processing circuitry, the at least one variable regarding the state of the brake fluid in the brake system based on the at least one determined volume flow variable and the at least one determined pressure difference variable; and outputting, by a control device of the brake system, a control signal to control operation of the brake system as a function of the determined at least one variable regarding the state of the brake fluid in the brake system.

2. The method of claim 1, wherein the at least one variable includes at least one of a viscosity of the brake fluid, a temperature of the brake fluid, a water content of the brake fluid, an aging state of the brake fluid, and a composition of the brake fluid.

3. The method of claim 1, wherein:
the volume flow Q is the volume flow variable and is determined as $Q = v_0 * \Phi$; and
$\Phi$ is a braking surface of the rod piston.

4. The method of claim 1, wherein:
the pedal travel of the brake pedal is the pedal travel variable; and
the simulator internal pressure is the simulator internal pressure variable and is determined additionally based on a pedal-travel to simulator-internal-pressure relationship specified for the simulator.

5. The method of claim 1, wherein:
the at least one variable is a viscosity of the brake fluid;
the volume flow Q is the volume flow variable;
the pressure difference is the pressure difference variable and is between the admission pressure and the simulator internal pressure;
at least one single value $v_i$ is determined as $$v_i = \frac{1}{A}\left(\frac{\Delta p}{\rho * Q} - B * Q\right);$$

$\rho$ is a density of the brake fluid;
A is a specified pressure loss parameter; and
B is a specified pressure drop parameter.

6. The method of claim 5, wherein the viscosity of the brake fluid is determined as an average value of multiple single values $v_i$.

7. The method of claim 5, wherein the pressure loss parameter A and the pressure drop parameter B are specified by using two calibration measurements using brake fluids of different viscosities v.

8. The method of claim 1, wherein the control signal controls flow of the brake fluid during operation of the brake system.

9. The method of claim 1, wherein the control signal controls a response of the brake pedal to flow of the brake fluid during operation of the brake system.

10. The method of claim 1, further comprising sensing, by at least one sensor, the at least one of the displacement speed of the brake pedal or the displacement speed of the rod piston.

11. The method of claim 1, further comprising sensing, by at least one sensor, the pedal travel of the brake pedal.

12. The method of claim 1, further comprising sensing, by at least one sensor, the admission pressure.

13. A device for ascertaining at least one variable regarding a state of a brake fluid in a brake system of a vehicle, the device comprising:
a sensor arrangement;
processing circuitry communicatively coupled to the sensor arrangement, wherein the processing circuitry is configured to:
determine a volume flow variable regarding a volume flow Q of the brake fluid, which flows via a simulator separation valve into a simulator of the brake system during an actuation of a brake pedal of the brake system, based on at least one displacement speed variable, obtained based on input from the sensor arrangement, regarding at least one of: (a) a displacement speed $v_p$ of the brake pedal of the brake system due to the actuation of the brake pedal, or (b) a displacement speed $v_0$ of a rod piston of the brake system displaced by the actuation of the brake pedal;
determine a simulator internal pressure variable regarding a simulator internal pressure increased as a result of the volume flow Q into the simulator based on at least one pedal travel variable, obtained based on input from the sensor arrangement, regarding a pedal travel of the brake pedal; and
determine a pressure difference variable regarding a pressure difference $\Delta p$, which prevails at the simulator separation valve, through which the volume flow Q flows, based on the simulator internal pressure variable determined for the respective volume flow Q and an admission pressure variable, obtained based on input from the sensor arrangement and ascertained for the respective volume flow Q regarding an admission pressure prevailing at the simulator separation valve, through which volume flow Q flows, on a side that is facing away from the simulator; and
determine the at least one variable regarding the state of the brake fluid in the brake system based on the at least one determined volume flow variable and the at least one determined pressure difference variable; and
a control device to output a control signal to control operation of the brake system as a function of the determined at least one variable regarding the state of the bake fluid in the brake system.

14. The device of claim 13, wherein the at least one variable includes at least one of a viscosity of the brake fluid, a temperature of the brake fluid, a water content of the brake fluid, an aging state of the brake fluid, and a composition of the brake fluid.

15. The device of claim 13, wherein:
the volume flow Q is the volume flow variable and the processing circuitry is configured to determine the volume flow Q as $Q = v_0 * \Phi$; and
$\Phi$ is a braking surface of the rod piston.

16. The device of claim 13, wherein:
the pedal travel of the brake pedal is the pedal travel variable; and
the simulator internal pressure is the simulator internal pressure variable, and the processing circuitry is configured to determine the simulator internal pressure additionally based on a pedal-travel to simulator-internal-pressure relationship specified for the simulator.

17. The device of claim 13, wherein:
the at least one variable is a viscosity of the brake fluid;
the volume flow Q is the volume flow variable;
the pressure difference is the pressure difference variable and is between the admission pressure and the simulator internal pressure;
the processing circuitry is configured to determine at least one single value $v_i$ as $$v_i = \frac{1}{A}\left(\frac{\Delta p}{\rho * Q} - B * Q\right);$$

$\rho$ is a density of the brake fluid;
A is a specified pressure loss parameter; and
B is a specified pressure drop parameter.

18. The device of claim 17, wherein the processing circuitry is configured to determine the viscosity of the brake fluid as an average value of multiple single values $v_i$.

19. The device of claim 18, wherein, at most, a single one of the values $v_i$ is determined during any single actuation of the brake pedal.

20. A brake system for a vehicle comprising a device for ascertaining at least one variable regarding a state of a brake fluid in a brake system of a vehicle, the device comprising:
a sensor arrangement;
processing circuitry communicatively coupled to the sensor arrangement, wherein the processing circuitry is configured to:
determine a volume flow variable regarding a volume flow Q of the brake fluid, which flows via a simulator separation valve into a simulator of the brake system during an actuation of a brake pedal of the brake system, based on at least one displacement speed variable, obtained based on input from the sensor arrangement, regarding at least one of: (a) a displacement speed $v_p$ of the brake pedal of the brake system due to the actuation of the brake pedal, or (b) a displacement speed $v_0$ of a rod piston of the brake system displaced by the actuation of the brake pedal;
determine a simulator internal pressure variable regarding a simulator internal pressure increased as a result of the volume flow Q into the simulator based on at least one pedal travel variable, obtained based on input from the sensor arrangement, regarding a pedal travel of the brake pedal;
determine a pressure difference variable regarding a pressure difference $\Delta p$, which prevails at the simulator separation valve, through which the volume flow Q flows, based on the simulator internal pressure variable determined for the respective volume flow Q and an admission pressure variable, obtained based on input from the sensor arrangement and ascertained for the respective volume flow Q regarding an admission pressure prevailing at the simulator separation valve, through which volume flow Q flows, on a side that is facing away from the simulator; and determine the at least one variable regarding the state of the brake fluid in the brake system based on the at least one determined volume flow variable and the at least one determined pressure difference variable; and a control device to output a control signal to control operation of the brake system as a function of the determined at least one variable regarding the state of the brake fluid in the brake system.

* * * * *